United States Patent
Huang et al.

(10) Patent No.: US 10,962,530 B2
(45) Date of Patent: Mar. 30, 2021

(54) MOLECULAR PROBE FOR SIGNAL AMPLIFICATION AND KIT AND ASSAY USING THE SAME

(71) Applicants: NATIONAL CHENG KUNG UNIVERSITY, Tainan (TW); NATIONAL CHENG KUNG UNIVERSITY HOSPITAL, Tainan (TW)

(72) Inventors: Wei-Lun Huang, Tainan (TW); Wu-Chou Su, Tainan (TW); Hai-Wen Chen, Tainan (TW); Wei-Pang Chung, Tainan (TW); I-Ting Chiang, Tainan (TW); Te-Fu Yeh, Tainan (TW); Hsisheng Teng, Tainan (TW); Liang-Che Chen, Tainan (TW)

(73) Assignees: NATIONAL CHENG KUNG UNIVERSITY, Tainan (TW); NATIONAL CHENG KUNG UNIVERSITY HOSPITAL, Tainan (TW)

( * ) Notice: Subject to any disclaimer, the term of this patent is extended or adjusted under 35 U.S.C. 154(b) by 421 days.

(21) Appl. No.: 15/842,857

(22) Filed: Dec. 14, 2017

(65) Prior Publication Data

US 2018/0128820 A1 May 10, 2018

Related U.S. Application Data

(63) Continuation-in-part of application No. 15/462,920, filed on Mar. 20, 2017.
(Continued)

(51) Int. Cl.
*G01N 33/542* (2006.01)
*G01N 33/58* (2006.01)

(52) U.S. Cl.
CPC ......... *G01N 33/542* (2013.01); *G01N 33/581* (2013.01); *G01N 33/588* (2013.01); *G01N 2333/5412* (2013.01)

(58) Field of Classification Search
CPC .. G01N 33/581; G01N 33/542; G01N 33/588; G01N 2333/5412
See application file for complete search history.

(56) References Cited

U.S. PATENT DOCUMENTS 7,923,240 B2 4/2011 Su
2016/0087148 A1 3/2016 Huang et al.

FOREIGN PATENT DOCUMENTS

CN 103649754 A 3/2014
TW 201612502 A 4/2016
WO 03/104424 A2 12/2003

OTHER PUBLICATIONS

Shu et al. Cobalt-porphyrin-platinum-functionalized reduced graphene oxide hybrid nanostructures: A novel peroxidase mimetic system for improved electrochemical immunoassay. Sci. Rep. 2015, vol. 5, Article # 15113, pp. 1-11. (Year: 2015).*

(Continued)

*Primary Examiner* — Shafiqul Haq
(74) *Attorney, Agent, or Firm* — ScienBiziP, P.C.

(57) ABSTRACT

A molecular probe includes a detector molecule specific to a target molecule, and at least one label linked covalently or non-covalently to the detector molecule. The label includes a catalyst for generating electrons and/or mediators from a solution. The catalyst includes a nanomaterial, an enzyme, a metal, and/or a metal complex. The mediators can accumulate in the solution for a period of time. The detector molecule and the target molecule interact with each other by a protein based or nucleotide sequence based interaction. The mediators participate in a chemical reaction that generates a signal that may be a change in optical, electromagnetic, thermodynamic or mechanical properties. Generation efficiency of the mediators is enhanced by providing an energy to the solution. The molecular probe may be used with a molecular detection assay performed on a surface. A method for assaying the target molecule using the molecular probe is also provided.

4 Claims, 14 Drawing Sheets

Related U.S. Application Data

(60) Provisional application No. 62/482,198, filed on Apr. 6, 2017, provisional application No. 62/311,194, filed on Mar. 21, 2016.

(56) References Cited

OTHER PUBLICATIONS

Lee et al. Graphene-based chemiluminescence resonance energy transfer for homogeneous immunoassay. 2012, vol. 6, No. 4, pp. 2978-2983. (Year: 2012).*

Yuan Zhou et al: "Chemiluminescence immunoassay for the rapid and sensitive detection of antibody against porcine parvovirus by using horseradish peroxidase/detection antibody-coated gold nanoparticles as nanoprobes : Porcine parvovirus antibody detected by chemiluminescence immunoassay", Luminescence: The Journal of Biological and Chemical Luminescence, vol. 29, No. 4, Jul. 5, 2013 (Jul. 5, 2013), pp. 338-343, XP055475202, GB.

Ron Gill et al: "Optical Detection of Glucose and Acetylcholine Esterase Inhibitors by H2O2-Sensitive CdSe/ZnS Quantum Dots", Angewandte Chemie International Edition, vol. 47, No. 9, Feb. 15, 2008 (Feb. 15, 2008), pp. 1676-1679, XP055475452.

Yi Liang et al., "Fluorescence ELISA for sensitive detection of ochratoxin A based on glucose oxidase-mediated fluorescence quenching of CdTe QDs", Jun. 18, 2016, Anal Chim Acta, Sep. 14, 2016; 936:195-201, Epub Jun. 18, 2016.

Yifei Zhang et al., "Proximity does not contribute to activity enhancement in the glucose oxidase-horseradish peroxidase cascade", Nature Communications vol. 7, Article No. 13982 (2016), Published: Dec. 22, 2016.

* cited by examiner

MOLECULAR PROBE FOR SIGNAL AMPLIFICATION AND KIT AND ASSAY USING THE SAME

CROSS-REFERENCE TO RELATED APPLICATION

The present disclosure claims priority to U.S. provisional patent application No. 62/482,198, filed on Apr. 6, 2017, and is a continuation-in-part of U.S. non-provisional patent application Ser. No. 15/462,920, filed on Mar. 20, 2017, which claims priority to U.S. provisional patent application No. 62/311,194, filed on Mar. 21, 2016, the entirety of which are incorporated herein by reference.

FIELD OF THE INVENTION

The present disclosure relates to a molecular probe, a kit and a method for signal amplification, and more particularly to a molecular probe, a kit and a method for amplifying detection signals of a molecular detection assay.

BACKGROUND OF THE INVENTION

Conventional immunoassays, as illustrated in FIG. 1, utilize the ability of a pair of capture antibody and detection antibody to recognize and bind a target molecule to detect the presence of the target molecule in a solution, and have been a useful tool for laboratory tests and medical diagnosis, as well as food and environmental testing. To quantify the target molecule, the detection antibody is typically linked to a detectable label that can or can be induced to illuminate, emit radiation, or produce color change or to a catalyst that can cause any of the detectable changes to generate a measurable signal in response to the binding of the antibody to the target molecule.

Under such mechanistic setting, however, the detection of one target molecule corresponds to only one measurable signal at a time (for example, in luminescent immunoassays, one horseradish peroxidase (HRP) can only react with one luminol molecule at a time to generate one photon, which fades away immediately after generation), thus resulting in weak signal intensity and poor detection sensitivity and accuracy. Consequently, a significant percentage of conventional immunoassays have known to cause misdiagnosis and mistreatment.

BRIEF SUMMARY OF THE INVENTION

To improve sensitivity and accuracy of existing molecular assays, an embodiment of the present invention provides a molecular probe that includes a detector molecule specific to a target molecule, and at least one label linked covalently or non-covalently to the detector molecule. The label includes a catalyst for generating electrons and/or mediators from a solution.

Preferably, the catalyst of the label includes at least one of a nanomaterial, an enzyme, a metal, and a metal complex. The nanomaterial includes nanoparticles, two-dimensional nanostructures, and bulk nanostructured materials. The nanoparticles include metal nanoparticles, fullerenes, and quantum dots. The quantum dots include metal quantum dots, graphene quantum dots, graphene oxide quantum dots, and carbon quantum dots.

Preferably, the mediators generated by the catalyst are capable of accumulating in the solution for a period of time.

Preferably, the mediators can participate in a chemical reaction that generates a signal that includes a change in optical properties, electromagnetic properties, thermodynamic properties or mechanical properties.

Preferably, the mediators generated by the catalyst include at least one of reactive oxygen species, reactive nitrogen species, lipid peroxides or lipid oxidation products, tripropylamine (TPA), intermediate valence compounds, 3,3',5,5'-tetra-methylbenzidine (TMB), nitroxide-based persistent radicals, radical adducts, alpha-phenyl N-tertiary-butyl nitrone (PBN), 5,5-dimethyl-pyrroline N-oxide (DMPO), glutathione, glutathione disulfide, nicotinamide adenine dinucleotide (NAD/NADH), nicotinamide adenine dinucleotide phosphate (NADP/NADPH) and C-nitroso spin traps.

Preferably, the efficiency of generation of the mediators by the catalyst is enhanced by providing an energy to the solution. The energy may include a chemical energy, a radiant energy, a thermal energy, an electrical energy, a magnetic energy, an electromagnetic energy, a sound wave energy, a mechanical energy, or any combination thereof.

Preferably, the detector molecule and the target molecule interact with each other by a protein based interaction or a nucleotide sequence based interaction. The protein based interaction includes a ligand-receptor interaction or an antibody-antigen interaction.

Preferably, the molecular probe is used with a molecular detection assay that is performed on a surface.

Another embodiment of the present invention provides a method for assaying a target molecule. The method includes the steps of: letting a plurality of the aforementioned molecular probes bind a plurality of the target molecule in a solution; letting the solution stand for a period of time; adding a plurality of reactants for a chemical reaction to the solution; and measuring signals generated by the chemical reaction.

Preferably, the step of letting the solution stand for a period of time further include a step of: providing an energy to the solution.

In sum, the present invention according to the aforementioned embodiments amplifies detection signals or obtains amplified detection signals of molecular detection assays by labeling detector molecules with one or more catalysts that are capable of generating mediators from a solution. The mediators can stably accumulate in the solution for a period of time to continuously participate in the chemical reaction of the molecular detection assay, thereby resulting in significantly amplified signals (that is, an "one-to-many" amplification) in response to detection of the target molecule. Therefore, the present invention effectively improves the detection sensitivity of existing assays for little or reduced cost. Additionally, as the electrons and mediators can be generated simultaneously, the present invention provides at least two types of measurable signals, thus offering the possibility of reconfirming or double checking the detected signals so as to ensure accuracy of the molecular detection.

BRIEF DESCRIPTION OF THE DRAWINGS

The accompanying drawings illustrate one or more embodiments of the present invention and, together with the written description, explain the principles of the present invention. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
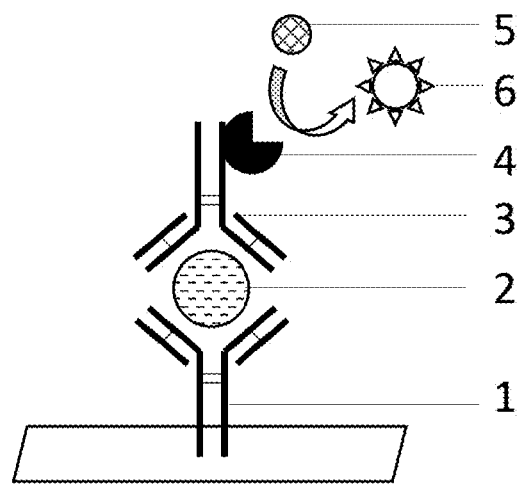
FIG. 1 is a schematic illustration of the concepts of a conventional molecular detection assay in accordance with the prior art.

The present invention will now be described more fully hereinafter with reference to the accompanying drawings illustrating various exemplary embodiments of the invention. The present invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

The term "molecular detection assay" described herein refers to a test that measures the presence and/or concentration of a target molecule (ie. an analyte) in a solution (for example, a biological fluid). As exemplified in FIG. 1, components of a typical molecular detection assay include a capture antibody 1 specific to the target molecule 2 (ie. having affinity or specific properties to the target molecule that allows specific binding thereof to the target molecule), and a detection antibody 3 also specific to the target molecule and linked with a tag 4 that catalyzes a chemical reaction to generate a detectable change when in contact with a reagent or reactant 5, to result in a measurable signal 6 in response to the binding of the detection antibody 3 to the target molecule 2.

The chemical reaction performed by the molecular detection assay may be a reduction-oxidation (redox) reaction, a photochemical reaction, an electrochemical reaction, a photoelectrochemical reaction, or other reaction that generates a measurable signal. The measurable signal may be in the form of a change in optical properties, electromagnetic properties, thermodynamic properties or mechanical properties. More specifically, the optical properties may include, but are not limited to, luminescent intensity, fluorescent intensity, color, luminescence wavelength profile, fluorescence wavelength profile, and optical wavelength profile. The electromagnetic properties may include, but are not limited to, electric current intensity, electric potential, conductivity, electrical charge, electric voltage, and relative permittivity. The thermodynamic properties may include, but are not limited to, temperature. The mechanical properties may include, but are not limited to, optical density (eg. light absorbance), resonance frequency, oscillation frequency, surface acoustic wave, piezoelectricity, and implant stability quotient.

The signal generated by the chemical reaction may be detectable by a potentiostat, galvanostat, cyclic voltammeter, electrochemical analyzer, electrochromic analyzer, fluorescence spectroscope, chemiluminescence spectroscope, electrochemiluminescence spectroscope, photochemiluminescence spectroscope, photoelectrochemiluminescence spectroscope, amperometric sensor, conductivity meter, pyrometer, piezoelectric sensor, resonance frequency analyzer, voltmeter, potentiometer, oscilloscope, Raman spectrometer, surface acoustic wave sensor, or quartz crystal microbalance.

Reactants of the chemical reaction may include luminol, isoluminol, aridinium ester, tris(2,2'-bipyridyl) ruthenium (II), $Ru(bpy)_3^{2+}$, 3-(2'-spiroadamantane)-4-methoxy-4-(3"-phosphoryloxy)phenyl-1,2-dioxetane (AMPPD), 3-(2'-spiroadamantane)-4-methoxy-4-(3"-beta-D'-galactopyranoyloxy)phenyl-1,2-dioxetane (AMPGD), Amplex Red reagent (10-acetyl-3,7-dihydroxyphenoxazine), luciferin, lucigenin, peroxidase. *Anthromyces ramosus* peroxidase (ARP), horseradish peroxidase (HRP), hydrolase, alkaline phosphatase (ALP), glucose oxidase, beta-D-galactosidase, glucose-6-phosphate dehydrogenase, luciferase, gold nanoparticle, hemin, metal complexes (e.g., $Cu^{2+}$ and $Fe^{3+}$ phthalocyanine complex), or any combination thereof.

Furthermore, the capture antibody 1 can be immobilized onto a surface, allowing the molecular detection assay to be performed on a dish, a well, a cube, a tube, a capillary, an electrode, a chamber, a membrane, a particle, a detector, a microtiter plate, a microchip, a semiconductor sensor chip or a cuvette. A few examples of the molecular detection assay include, but are not limited to, fluorescent assay, enzyme linked immunosorbent assay (ELISA), lateral flow assay, electrochemical assay, photochemical assay and photoelectrochemical assay.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
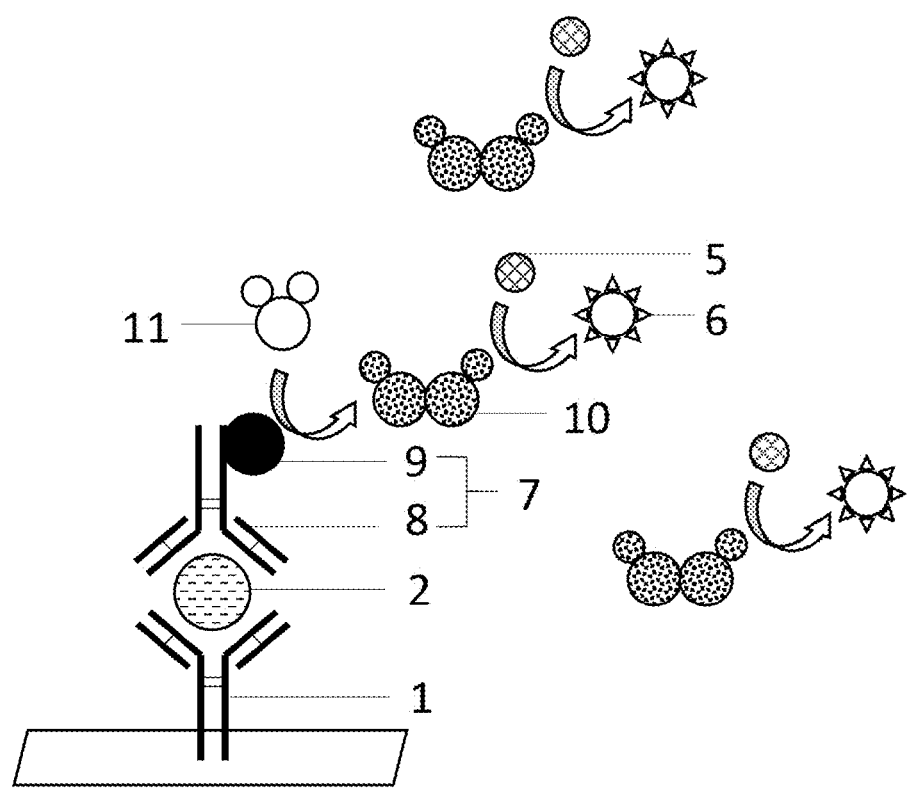
FIG. 2 is a schematic illustration of a molecular probe used in combination with a conventional molecular detection assay in accordance with an embodiment of the present invention.

Referring now to FIG. 2. A first aspect of the present invention provides a molecular probe for signal amplification. In an embodiment, the molecular probe 7 includes a detector molecule 8 and at least one label 9 linked to the detector molecule. The label 9 is linked to the detector molecule 8 covalently, by for example an ester bond, peptide bond, or thioester bond, or non-covalently, by for example hydrogen bond or π-π interaction. The label 9 includes a catalyst that can generate electrons and/or mediators 10 from a solution. The detector molecule 8 may be an antibody, an antigen, a ligand, a receptor or a nucleotide sequence that is specific to (ie., capable of specific binding to) a target molecule 2. The target molecule 2 may be an organic compound, an inorganic compound, or a biological molecule. Preferably, the organic compound is an aromatic compound, alcohol, aldehyde, ketone, acid, amine, urea, or a polymer or complex thereof; the inorganic compound is dodecaborate, nitride, metal containing complex; and the biological molecule is amino acids, nucleotides, lipids, saccharides, peptides, nucleic acid, polysaccharides, vitamins, hormones, or a polymer or complex thereof.

The detector molecule 8 and the target molecule 9 selectively interact with each other by selective molecular binding. The selective molecular binding may be a protein based interaction, a nucleotide sequence based interaction, or a combination thereof. The protein based interaction may include a ligand-receptor interaction or an antibody-antigen interaction. More specifically, in some embodiments, the ligand-receptor interaction includes, but is not limited to, an interaction between protein and lipid (eg. annexin A5 and phosphatidylserine), an interaction between protein and glycan/polysaccharide (eg. intelectins and microbial glycans), an interaction between protein and metals (eg. ferritin and iron) or an interaction between protein and small molecules (eg. epidermal growth factor receptor (EGFR) and gefitinib; or streptavidin and biotin). In some embodiments, the antibody-antigen interaction includes, but is not limited to, an interaction between DNA and antibody (eg. anti-dsDNA antibodies), an interaction between small molecules and antibody (eg. anti-aflatoxin antibodies), an interaction between lipids and antibody (eg. anti-phospholipid antibodies), an interaction between organic compounds and antibody (eg. anti-chlorophenols antibodies), an interaction between inorganic compounds and antibody (eg. anti-mercaptoundecahydrododecaborate (anti-BSH) antibodies), or an interaction between environmental pollutants or food contaminants and antibody (eg. anti-linear alkylbenzene sulphonates). In some embodiments, the nucleotide sequence-based interaction includes, but is not limited to, an interaction between DNA/RNA oligos via complimentary sequences, an interaction between small molecules and aptamers (eg. anti-dopamine aptamers), an interaction between proteins and aptamers (eg. anti-thrombin aptamers), or an interaction between nucleic acids and aptamers (eg. anti-human immunodeficiency virus (anti-HIV) transacting responsive element aptamers). The aforementioned interactions may be detected by immunoassays, nucleic acid detection assays, lipid detection assays, or saccharide detection assays.

The catalyst on the label 9 may be at least one of a nanomaterial, an enzyme, a metal and a metal complex. The nanomaterial may include two-dimensional nanostructures (e.g. graphene nanosheet and graphene oxide (GO) nanosheet), bulk nanostructured materials (e.g. nanoporous materials, nanocomposites, and nanocrystalline materials), and nanoparticles (eg. Au nanoparticles, Ag nanoparticles, Pt nanoparticles, Fe nanoparticles, FeAu nanoparticles, FePt nanoparticles, $TiO_2$ nanoparticles, and quantum dots (QDs)). The quantum dots may include, but are not limited to, core-type quantum dots, core-shell quantum dots, alloyed quantum dots, CdTe QDs, CdSe QDs, CdS QDs, ZnS QDs, PbS QDs, HgS QDs, PbSe QDs, graphene quantum dot (GQDs), graphene oxide quantum dot (GOQDs), carbon quantum dots (CQDs), InAs/ZnSe QDs, InAs/CdSe QDs, InAs/InP QDs, Cu:InP/ZnSe QDs, $InAs_xP_{1-x}$/InP/ZnSe QDs). The enzyme may include, but is not limited to, peroxidase, oxidase or derivatives thereof, such as *Anthromyces ramosus* peroxidase (ARP), horseradish peroxidase (HRP), catalase, glutathione peroxidase, nicotinamide adenine dinucleotide phosphate (NADPH) oxidase, glucose oxidase, cytochrome P450 oxidase, L-gluconolactone oxidase, monoamine oxidase, or lysyl oxidase; hydrolase, alkaline phosphatase (ALP) or derivatives thereof; glucose oxidase or derivatives thereof, such as beta-D-galactosidase, glucose-6-phosphate dehydrogenase, superoxide dismutase, lipoxygenase or luciferase). The metals and metal complexes may include, but are not limited to, isolated single-atomic Ru, $Cu^{2+}$ phthalocyanine complex, $Fe^{3+}$ phthalocyanine complex, hemin, transition metal carbene complex, such as Grubbs' catalyst).

In some embodiments, the nanomaterial is further doped with Mg, O, N, P, B, Fe, Co, Ni, or other Groups IIA, IIIA, IVA, VA, VIA elements or transition element having an empty d orbital, preferably at a ratio of about 0 mole percent (mol %) to 50 mol %. The nanomaterial may also be functionalized with an amino group (—$NH_2$), a phosphite group (—$PO_3$), a carbonyl group (—CO), a hydroxyl group (—OH), a carboxyl group (—COOH), an acyl group, a boron atom (B), a hydrogen atom (H), a nitrogen atom (N), an oxygen atom (O), a sulfur atom (S), a phosphorus atom (P) or other Groups IIIA, IVA, VA, VIA, VIIA-element functional groups, preferably at a ratio of about 0 mol % to 50 mol %.

In some embodiments, the nanomaterial has a particle size ranging from about 0.34 nm to 100 nm, for example 0.34 nm, 0.5 nm, 1 nm, 3 nm, 5 nm, 10 nm, 15 nm, 20 nm, 25 nm, 30 nm, 35 nm, 40 nm, 45 nm, 50 nm, 55 nm or 60 nm. The shape of the nanomaterial is generally ball-shaped, pillar-shaped or disc-shaped. In some embodiments, the nanomaterial is GOQDs that are of a disc-shaped structure having a thickness ranging from about 0.34 nm to 20 nm, for example 0.34, 0.5, 1, 3, 5, 10, 15 or 20 nm.

Referring again to FIG. 2. The catalyst of the label 9 can generate electrons and/or mediators 10 from a solution at various temperatures (preferably at 4-56° C., or more preferably, at 4° C., 25° C., 37° C., or 50° C.), with or without application of an external energy. The mediators 10 may be at least one of reactive oxygen species (ROS; eg. organic hydroperoxide, organic peroxide, radical initiator, hydrogen peroxide ($H_2O_2$), hydroxyl anion, superoxide radical, hydroxyl radical, or ozone), reactive nitrogen species (eg. nitric oxide, nitrogen dioxide, or peroxynitrous acid), lipid peroxides or lipid oxidation products (eg. fatty acid radical or peroxyl-fatty acid radical), tripropylamine (TPA), intermediate valence compounds (eg. tin (II) chloride ($SnCl_2$), iron (II) sulfate ($FeSO_4$), carbon monoxide, ruthenium (IV) oxide ($RuO_2$), or titanium (III) chloride ($TiCl_3$)), 3,3',5,5'-tetra-methylbenzidine (TMB), nitroxide-based persistent radicals, radical adducts, alpha-phenyl N-tertiary-butyl nitrone (PBN), 5,5-dimethyl-pyrroline N-oxide (DMPO), glutathione, glutathione disulfide, nicotinamide adenine dinucleotide (NAD/NADH), nicotinamide adenine dinucleotide phosphate (NADP/NADPH), and C-nitroso spin traps (eg. 3,5-dibromo-4-nitrosobenzenesulfonic acid (DBNBS), 5-Diisopropoxyphosphoryl-5-methyl-1-pyrroline-N-oxide (DIPPMPO)).

The solution may be a gaseous solution, liquid solution, and a solid solution. If the solvent is a gas, only gases are dissolved under a given set of conditions. If the solvent is a liquid, almost all gases, liquids, and solids can be dissolved including gas in liquid, liquid in liquid, and solid in liquid. If the solvent is a solid, gases, liquids and solids can be dissolved including gas in solid, liquid in solid, and solid in solid. The liquid solution can also be further classified into polar and non-polar solutions.

The mediators can accumulate in the solution for a period of time ranging from a few seconds to several months to continuously participate in a chemical reaction that produces measurable signals 6, thereby obtaining amplified signals in response to detection of the target molecule 2. In other words, each one of the catalysts of the embodiments of the present invention can generate multiple mediators, each of which reacts with the reactants of the chemical reaction to result in simultaneous generation of multiple measurable signals, therefore achieving an "one-to-many" signal amplification mode.

The externally applied energy for enhancing the generation of the mediators may be a chemical energy, a radiant energy, a thermal energy, an electrical energy, a magnetic energy, an electromagnetic energy, a sound wave energy, a mechanical energy, or any combination thereof. The energy may be provided by a laser, a mercury lamp, a visible light, an ultraviolet light, an infrared light, an endoscopic light, an X-ray, an ultrasound, an electric field, a magnetic field, a nuclear magnetic resonance, a functional generator, a hot plate, or a light-emitting diode.

The molecular probe according to the embodiments of the present invention may be used with a molecular detection assay (eg. an ELISA, a lateral flow assay, a fluorescent assay, an electrochemical assay, a photochemical assay or a photoelectrochemical assay) to amplify detection signals of the molecular detection assay. More specifically, in some embodiments, the method for assaying a target molecule using the molecular probes includes the steps of: letting the molecular probes bind a plurality of the target molecule in a solution; letting the solution stand for a period of time; adding a plurality of reactants for a chemical reaction to the solution; and measuring signals generated by the chemical reaction. In the embodiments, the target molecules are immobilized on a surface prior to binding with the molecular probes, by interacting with capture antibodies or detector molecules via a protein based or nucleotide sequence based interaction. Therefore, after the molecular probes are let bind with the target molecules, the method may optionally include a step of: removing a portion of the molecular probes not bound to the target molecules, by for example repeatedly removing the solution and adding a fresh solution free of the target molecules or the molecular probes.

In other embodiments, the molecular probe 7 may be immobilized on the surface and the label 9 thereof can be activated by a conformational change or other mechanism upon binding of the target molecule 2.

Preferably, the final concentration of the labels 9 on the molecular probes 8 in the solution is at a range of about $1 \times 10^{-15}$ mg/mL to 500 mg/mL. The method may be performed on a surface, such as a dish, a well, a cube, a tube, a capillary, an electrode, a chamber, a membrane, a particle, a detector, a microtiter plate, a microchip, a semiconductor sensor chip or a cuvette.

In other embodiments, the molecular probe may be provided as a kit to be used with a molecular detection assay for amplifying signals of the molecular detection assay. In an embodiment, the kit includes a plurality of the aforementioned detector molecule, a plurality of the aforementioned catalyst-containing label, and one or more reagents for covalently or non-covalently conjugating the detector molecule and the catalyst-containing label. The detector molecular and the label are conjugated by addition of the reagents prior to performing the molecular detection assay.

In some embodiments, the kit further includes a redox enhancer. The redox enhancer may be a nutrient, a vitamin, an alkali salt or buffer, an organic compound, an inorganic compound, transition metal ions having an empty d, f, or g orbital or any combination thereof. The nutrient may include serum free Roswell Park Memorial Institute (RPMI) medium, serum free Dulbecco's modified eagle medium (DMEM), serum free minimum essential medium alpha (MEMα), serum free Ham's F12 medium, serum free Leibovitz L15 medium, serum free Hybri-Care medium or fetal bovine serum. The vitamin may include ascorbic acid, co-enzyme Q10, glutathione or astaxanthin. The alkali salt or buffer may be phosphate-buffered saline or polysulfide. The organic compound may include porphyrin, chlorophyll, histamine, methanol, ethanol, triethanolamine, lactic acid, urea, or other heterocyclic or macrocyclic compound with at least one hydroxyl group, carbonyl group, or nitrogen. The inorganic compound may include silver nitrate or sodium iodate. The transition metal ions having an empty d, f, or g orbital may include ferric ion, ferrous or potassium permanganate ($KMnO_4$), cobalt ion, nickel ion, or any combination thereof. Preferably, the redox enhancer is added to the kit at a concentration range of about $1\times10^{-12}$ volume per volume percent (v/v %) to 50 v/v % or about $1\times10^{-15}$ molar (M) to 10 M.

Figure 3:
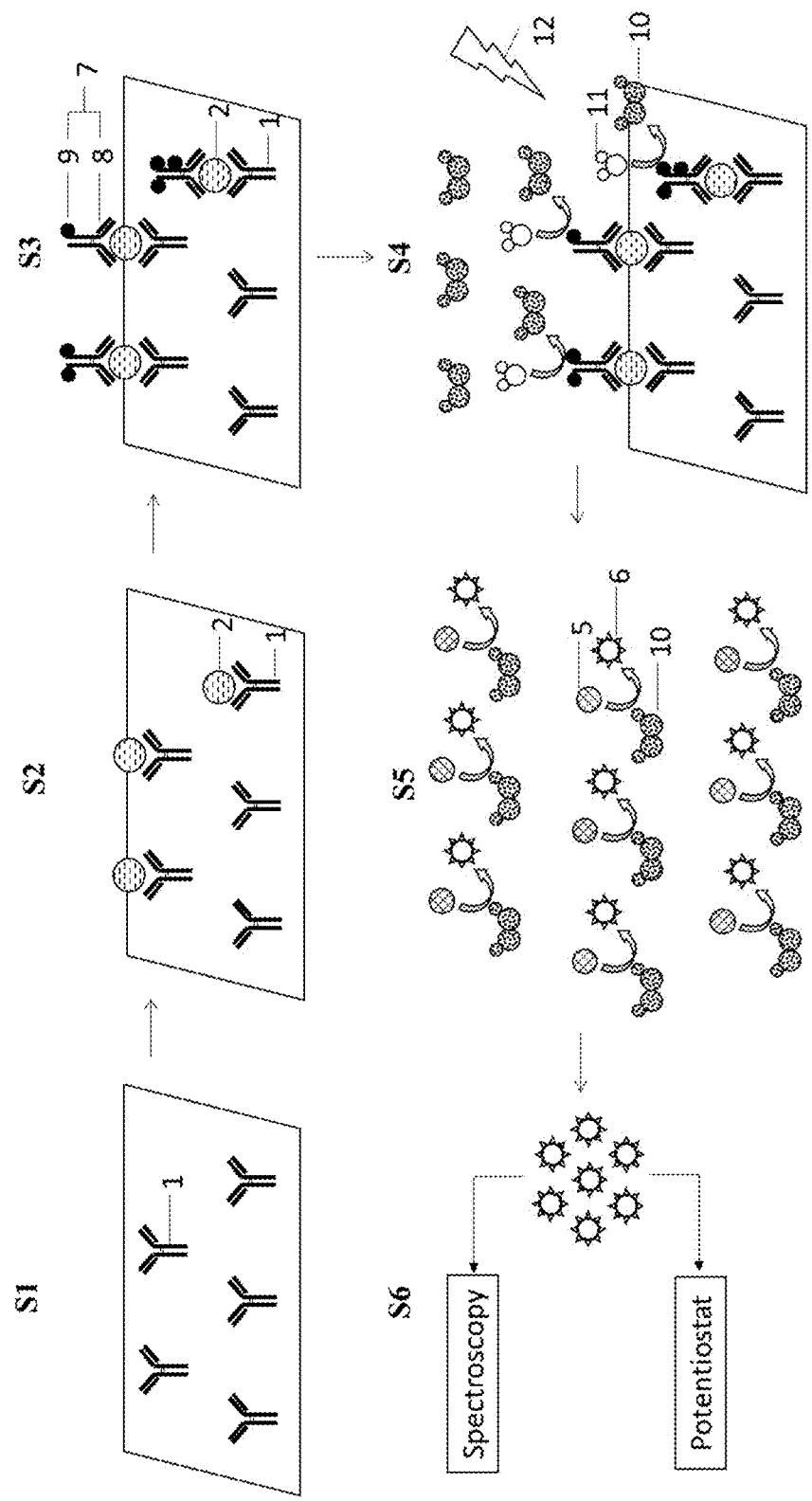
FIG. 3 is a schematic illustration of a method for amplifying detection signals of a molecular detection assay in accordance with an embodiment of the present invention.

Referring now to FIG. 3. Another aspect of the present invention provides a method for assaying a target molecule. In an embodiment, the method includes the steps of: (S1) providing a plurality of capture antibodies 1 immobilized on a surface; (S2) adding a sample containing a plurality of target molecules 2 in a solution to allow the capture antibodies 1 to bind the target molecules 2; (S3) adding a plurality of the aforementioned molecular probes 7 to allow the detector molecules 8 of the molecular probes 7 to bind the target molecules 2; (S4) letting the solution stand for a period of time to allow mediators 10 to be generated by the labels 9 of the molecular probes 7 and to accumulate in the solution; (S5) adding a plurality of reactants 5 to the solution to initiate a chemical reaction that produces measurable signals 6; and (S6) measuring the signals 6.

Preferably, the final concentration of the labels 9 on the molecular probes 8 in the solution is at a range of about $1\times10^{-15}$ mg/mL to 500 mg/mL. Meanwhile, when the molecular probes are added, the solution may contain all of the reagents and buffers necessary for performing the assay, except those required for performing the chemical reaction (for example, the reactants of the chemical reaction).

The mediators 10 generated by the labels 9 may be at least one of reactive oxygen species (ROS), reactive nitrogen species, lipid peroxides or lipid oxidation products, tripropylamine (TPA), intermediate valence compounds, 3,3',5,5'-tetra-methylbenzidine (TMB), nitroxide-based persistent radicals, radical adducts, alpha-phenyl N-tertiary-butyl nitrone (PBN), 5,5-dimethyl-pyrroline N-oxide (DMPO), glutathione, glutathione disulfide, NAD(H), NADP(H), and C-nitroso spin traps. The mediators can accumulate in the solution, preferably for a duration ranging from a few minutes to several weeks, to continuously participate in the chemical reaction, thereby achieving "one-to-many" signal amplification in response to detection of the target molecules 2. Preferably, prior to addition of the reactants 5, the solution containing the molecular probes and the immobilized target molecules is let stand at room temperature for 1 min. However, it is to be understood the present invention does not limit the duration for and temperature at which the solution is let stand; the embodiments of the present invention can function as long as the mediators are stably generated and accumulate in the solution.

In some embodiments, the measurable signals may be in the form of a change in change in optical properties, electromagnetic properties, thermodynamic properties or mechanical properties. For example, the optical properties may be luminescent intensity, fluorescent intensity, color, luminescence wavelength profile, fluorescence wavelength profile, or optical wavelength profile. The electromagnetic properties may be electric current intensity, electric potential, conductivity, electrical charge, electric voltage, or relative permittivity. The thermodynamic properties may include, but are not limited to, temperature. The mechanical properties may be optical density (eg. light absorbance), resonance frequency, oscillation frequency, surface acoustic wave, piezoelectricity, or implant stability quotient. In some embodiments, the signals may be detectable by a potentiostat, galvanostat, cyclic voltammeter, electrochemical analyzer, electrochromic analyzer, fluorescence spectroscope, chemiluminescence spectroscope, electrochemiluminescence spectroscope, photochemiluminescence spectroscope, photoelectrochemiluminescence spectroscopy, amperometric sensor, conductivity meter, pyrometer, piezoelectric sensor, resonance frequency analyzer, voltmeter, potentiometer, oscilloscope, Raman spectrometer, surface acoustic wave sensor, or quartz crystal microbalance.

In some embodiments, the method may be performed on a surface, such as a dish, a well, a cube, a tube, a capillary, an electrode, a chamber, a membrane, a particle, a detector, a microtiter plate, a microchip, a semiconductor sensor chip or a cuvette.

In an alternative embodiment, the method does not require the use of the capture antibodies. That is, the molecular probe 7 may be immobilized on the surface and the label 9 thereof can be activated by a conformational change or other mechanism upon binding of the target molecule 2.

In a preferred embodiment, the method for assaying a target molecule further includes a step of: providing an energy 12 to the solution when the solution is let stand for a period of time. The energy 12 may be a chemical energy, a radiant energy, a thermal energy, an electrical energy, a magnetic energy, an electromagnetic energy, a sound wave energy, a mechanical energy, or any combination thereof. The energy 12 may be provided by a laser, a mercury lamp, a visible light, an ultraviolet light, an infrared light, an endoscopic light, an X-ray, an ultrasound, an electric field, a magnetic field, a nuclear magnetic resonance, a functional generator, a hot plate, or a light-emitting diode. The energy should be sufficient to accelerate or facilitate the generation of electrons and/or mediators 10 by the labels 9 of the molecular probes 7. Preferably, the energy is provided to the solution by light exposure for a period of time (eg. 100 mW/cm$^{-2}$ of visible light for 20 sec) and/or by addition of a redox enhancer (eg. 10 mM of ascorbic acid).

More specifically, the radiant energy may be provided at a wavelength range of 1 pm to 1600 nm, or preferably 1 pm to 1 nm (for ionizing radiation), 10 nm to 400 nm (for ultraviolet radiation), 400 nm to 1000 nm (for visible light and infrared radiation) or any combination thereof. The radiant energy may be at a power range of about $1\times10^{-6}$ µW/cm$^2$ to 100 W/cm$^2$, or preferably 10 µW/cm$^2$ to 5 W/cm$^2$. The thermal energy may be provided at a power range of about $1\times10^{-6}$ µW/cm$^2$ to 100 W/cm$^2$, or preferably 10 µW/cm$^2$ to 5 W/cm$^2$. The electrical energy may be provided at an electric potential range of about 0.0001 V to 500 V, or preferably −5 V to 5V; the electrical energy may have a current response ranging from about $1\times10^{-15}$ A/cm$^2$ to 100 A/cm$^2$, or preferably $1\times10^{-12}$ to 10 A/cm$^2$. The magnetic energy may be provided at a power range of about $1\times10^{-6}$ µW/cm$^2$ to 100 W/cm$^2$, or preferably about 10

μW/cm² to 5 W/cm². The mechanical energy may preferably be an ultrasonic energy provided at a power range of about $1\times10^{-6}$ μW/cm² to 100 W/cm², or preferably about 10 μW/cm² to 5 W/cm².

Figure 4:
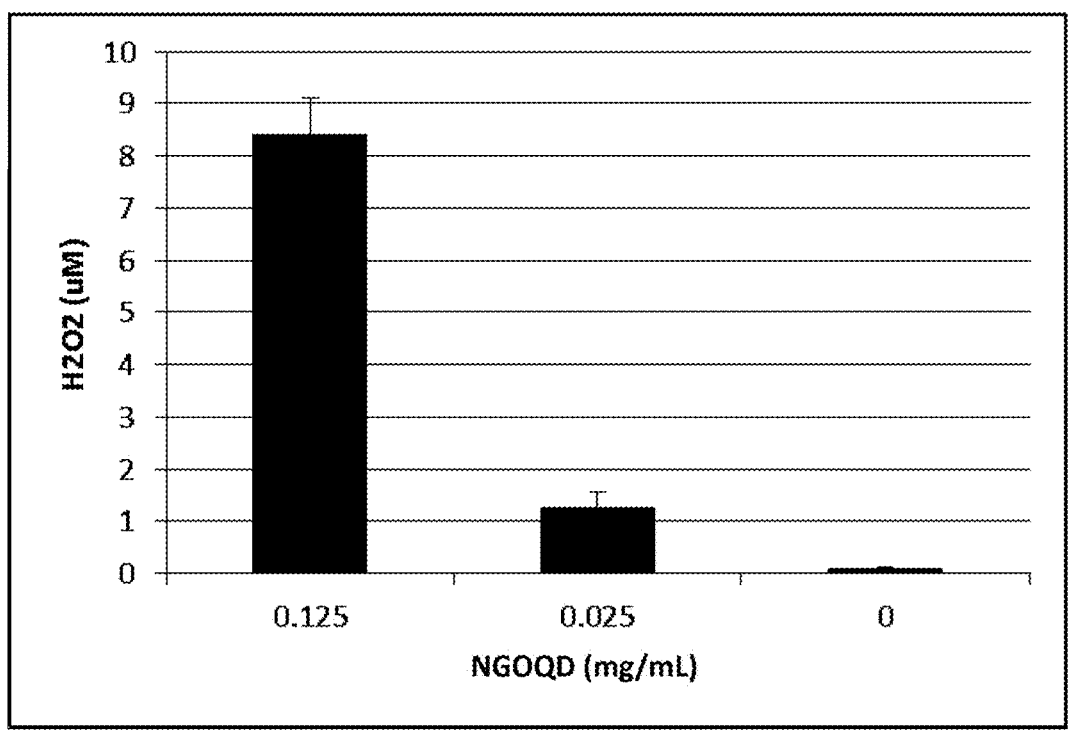
FIG. 4 is an experimental result showing the correlation between the concentrations of nitrogen-doped graphene oxide quantum dots (NGOQDs) and hydrogen peroxide ($H_2O_2$) in accordance with an embodiment of the present invention.

Referring now to FIG. 4. The amount of catalysts on the molecular probe of the embodiments of the present invention is demonstrated to correlate with the generation of mediators. In an experiment as shown in FIG. 4, the concentration of $H_2O_2$ in the solution was shown to increase with the concentration of NGOQDs, suggesting that NGOQDs can be triggered to generate $H_2O_2$ from the solution.

Figure 5A:
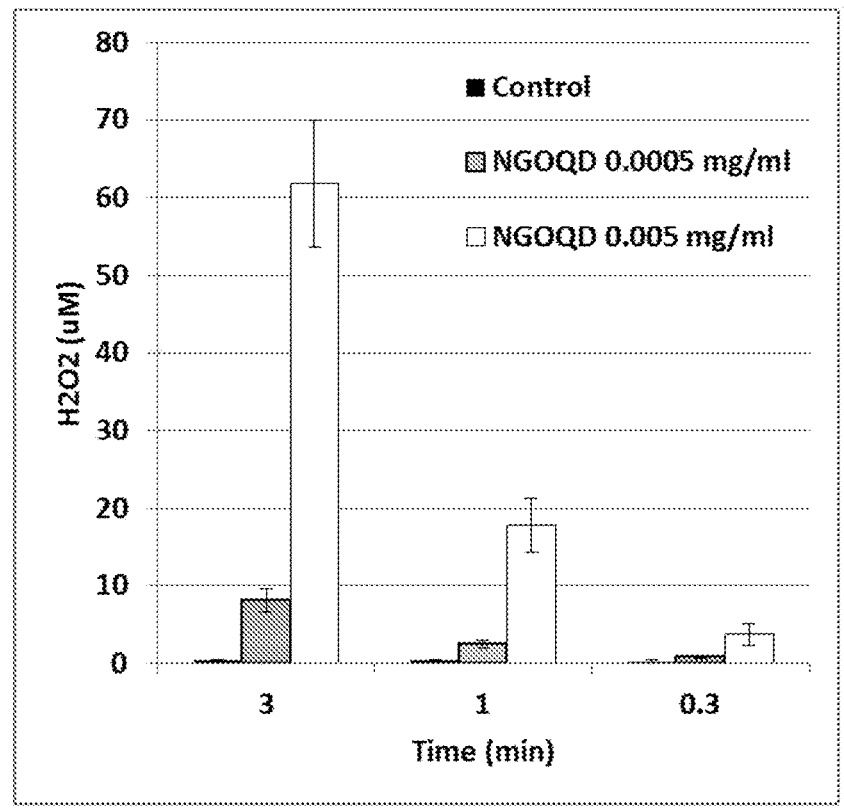
FIG. 5A is an experimental result showing the accumulation of $H_2O_2$ over time in accordance with an embodiment of the present invention.
Figure 5B:
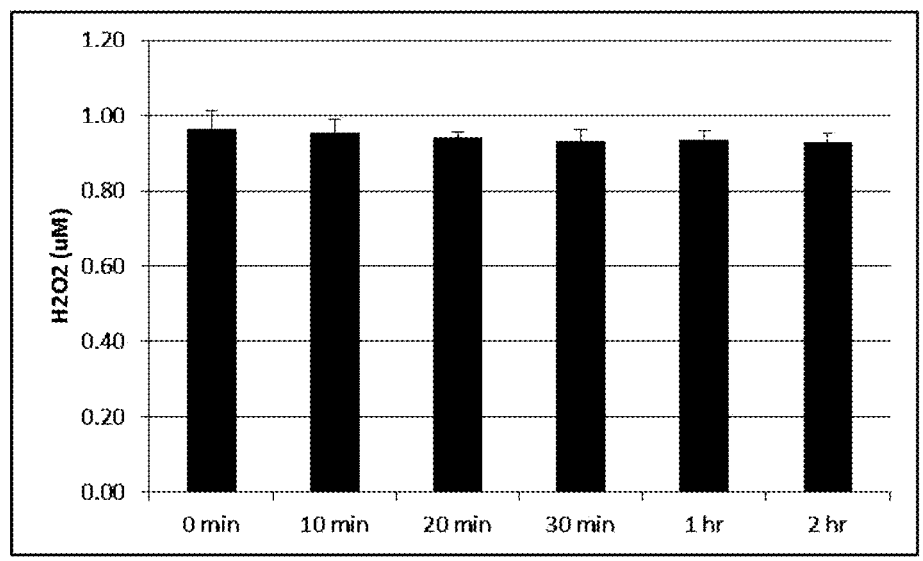
FIG. 5B is an experimental result showing the stability of $H_2O_2$ over time in accordance with an embodiment of the present invention.

Referring now to FIGS. 5A and 5B. The mediators generated according to the embodiments of the present invention are demonstrated to accumulate in the solution and sustain for an extended period of time. As shown in FIG. 5A, when a final concentration of 0.005 mg/mL of nitrogen doped graphene oxide quantum dots (NGOQDs) is added to an experimental assay, the concentration of $H_2O_2$ as determined by the commercially available Amplex® Red Hydrogen Peroxide/Peroxidase Assay Kit was shown to accumulate to over 60 μM in just 3 min. The accumulated $H_2O_2$ is also stable; as shown in FIG. 5B, 1 μM of $H_2O_2$ was demonstrated to be stably present in the assay mixture for at least 2 hours.

Figure 6A:
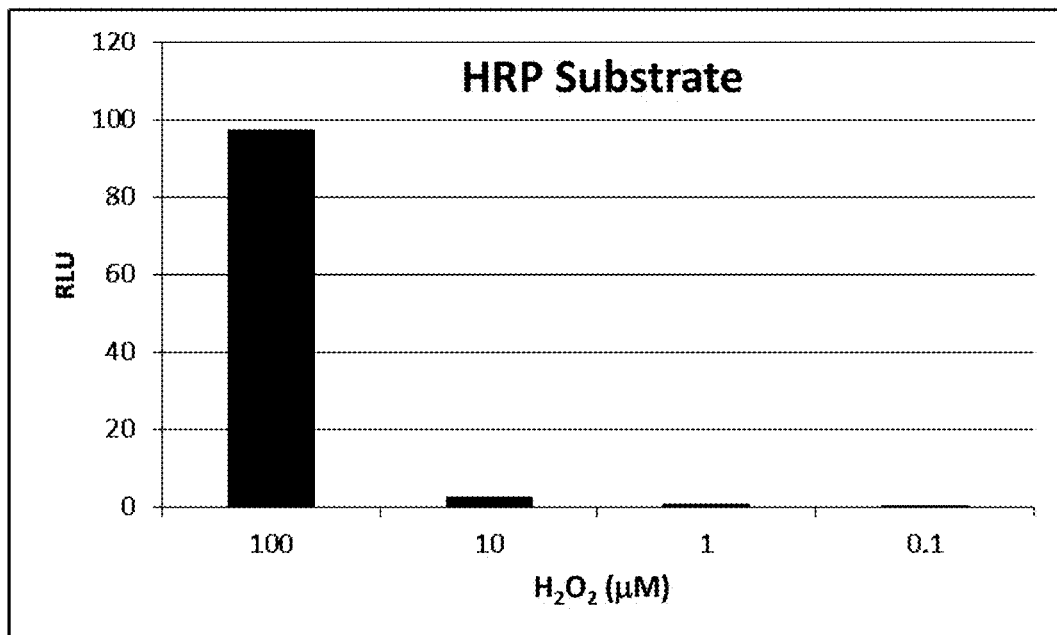
FIG. 6A is an experimental result showing the correlation between $H_2O_2$ concentration and intensity of chemiluminescent signals generated from a chemiluminescent HRP substrate in accordance with an embodiment of the present invention.
Figure 6B:
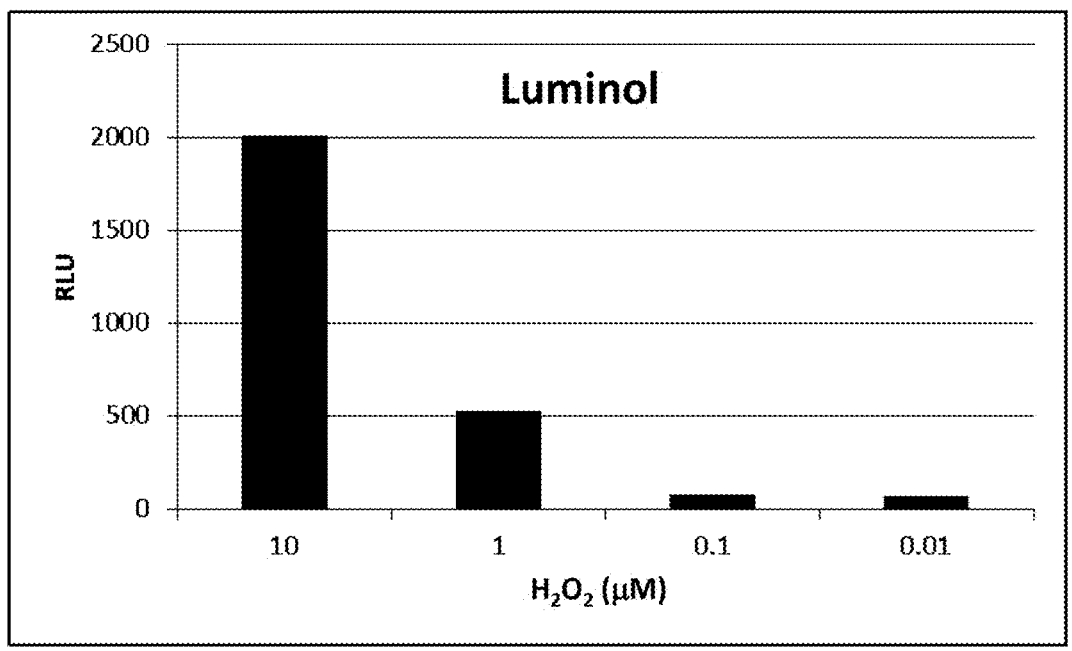
FIG. 6B is an experimental result showing the correlation between $H_2O_2$ concentration and intensity of chemiluminescent signals generated from luminol in accordance with an embodiment of the present invention.

Referring now to FIGS. 6A and 6B. The mediators generated according to the embodiments of the present invention are demonstrated to strongly associate with amplification of the luminescent signals. As shown in FIG. 6A, the intensity of the resulting chemiluminescence signals of an experimental assay using horseradish peroxide (HRP) and a chemiluminescent HRP substrate was shown to increase with the concentration of $H_2O_2$. Likewise, in another experiment as shown in FIG. 6B, the intensity of chemiluminescence signals generated from luminol was also shown to increase with the concentration of $H_2O_2$.

Figure 7A:
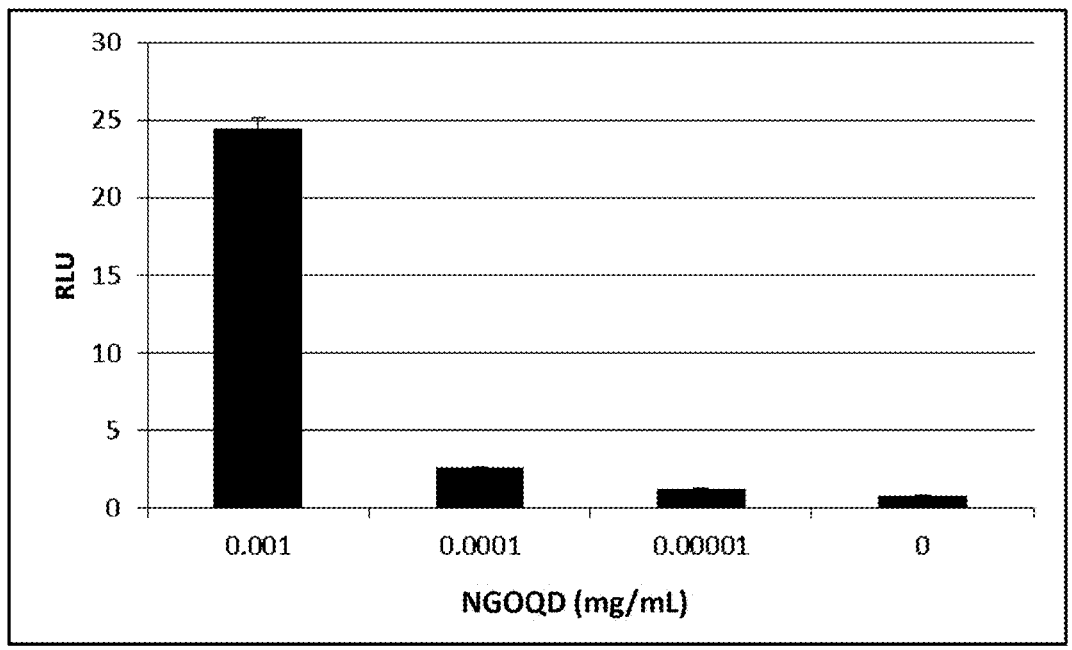
FIG. 7A is an experimental result showing the correlations between the concentrations of nitrogen-doped graphene oxide quantum dots (NGOQDs) and intensity of chemiluminescent signals in accordance with an embodiment of the present invention.
Figure 7B:
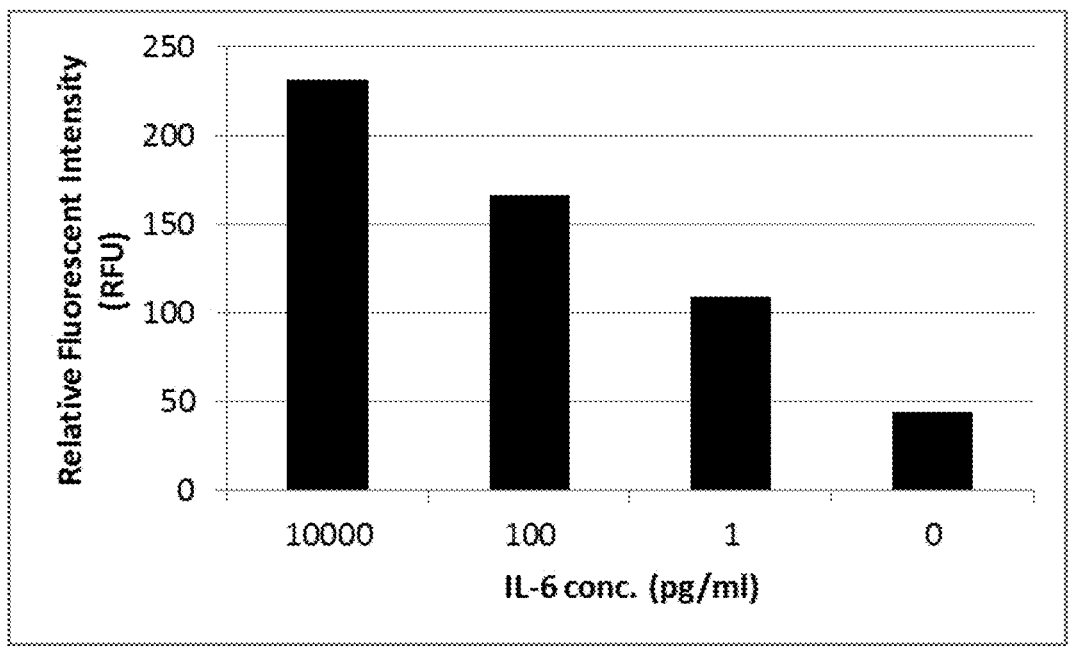
FIG. 7B is an experimental result showing the correlations between the concentrations of target molecule and intensity of chemiluminescent signals in accordance with an embodiment of the present invention.

Referring now to FIGS. 7A and 7B. The embodiments of the present invention are demonstrated to amplify detection signals of a sandwich immunoassay for detection of interleukin (IL-6). In an experiment, in which the label of the molecular probe included nitrogen doped graphene oxide quantum dots (NGOQDs) and the assay involved a luminescent reaction that uses a horseradish peroxidase (HRP) and a chemiluminescent HRP substrate, a NGOQD dose dependent increase in luminescence is observed after exposing the solution to 100 mW/cm⁻² of light for 20 sec, as shown in FIG. 7A. Meanwhile, as shown in FIG. 7B, the intensity of the resulting luminescence signals is also shown to correlate with the concentration of IL-6 in a sandwich immunoassay using molecular probes labeled with the NGOQDs.

Figure 8:
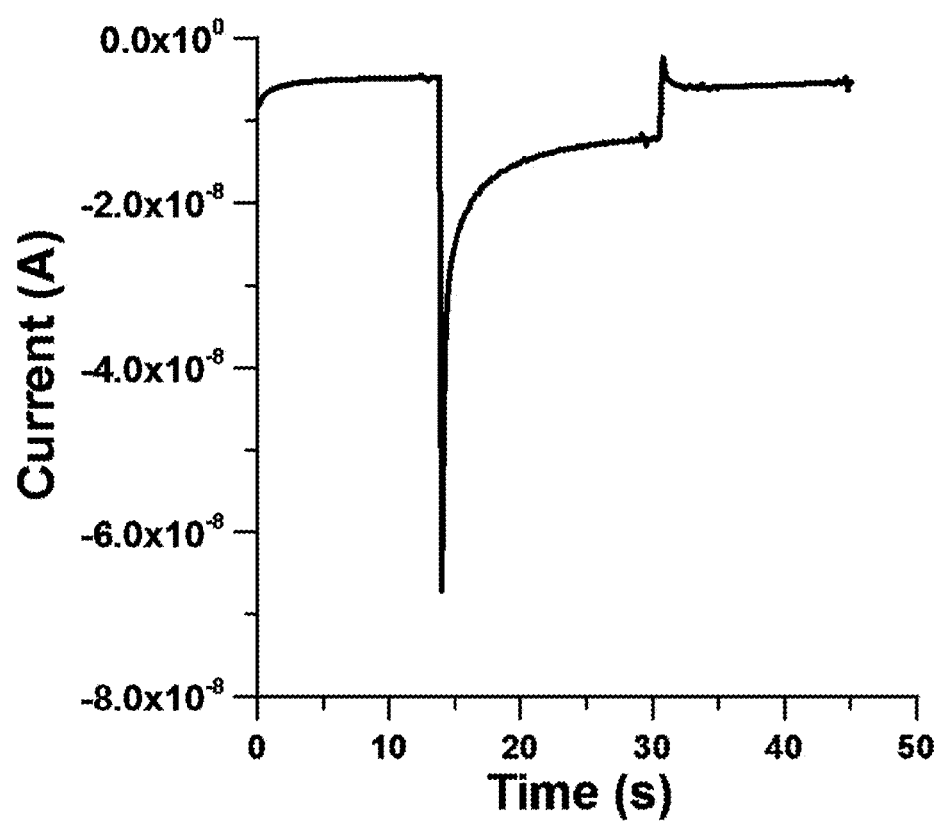
FIG. 8 is an experimental result showing the generation of electric currents in response to light exposure in accordance with an embodiment of the present invention.

Referring now to FIG. 8. The embodiments of the present invention are also demonstrated to generate electrons, and thus electric currents, in the molecular detection assay. In an experiment as shown in FIG. 8, an electric current was detected upon exposure of the solution containing NGOQD-labeled molecular probes to 100 mW/cm⁻² of light; the light was kept on for 20 seconds, during which the electric current continued to be generated but attenuated over time. Generation of the electric current stopped immediately after the light was switched off. Further, as electrons and mediators are demonstrated to be generated simultaneously by the catalyst on the molecular probe of the embodiments of the present invention, the result shown in FIG. 8 is also indicative of the timing of generation and relative quantity of the mediators (eg. $H_2O_2$).

Figure 9:
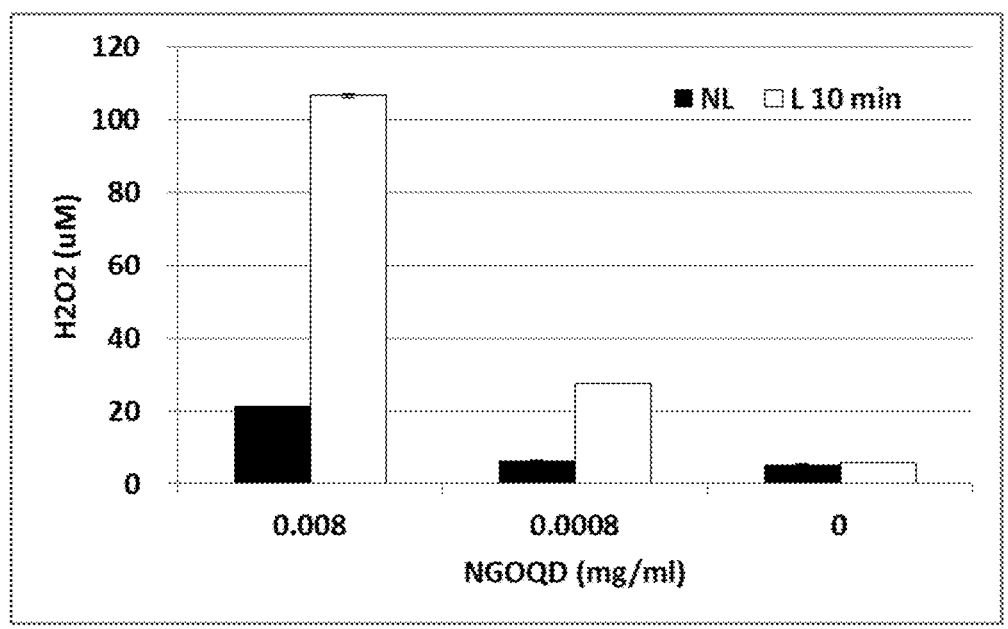
FIG. 9 is an experimental result showing the enhancement of generation efficiency of $H_2O_2$ by providing light energy in accordance with an embodiment of the present invention.

Referring now to FIG. 9. Efficiency of generation of the mediators according to the embodiments of the present invention are demonstrated to be enhanced by providing an energy (eg. light energy) to the solution. In an experiment as shown in FIG. 9, when providing 2 mM of ascorbic acid to a solution containing 0.008 mg/mL or 0.0008 mg/mL of NGOQD, the NGOQDs having been exposed to 100 mW/cm⁻² of light for 10 min (denoted L10 min in the figure) resulted in production of approximately 5 folds of $H_2O_2$, as compared to those without light exposure (denoted NL in the figure).

Figure 10:
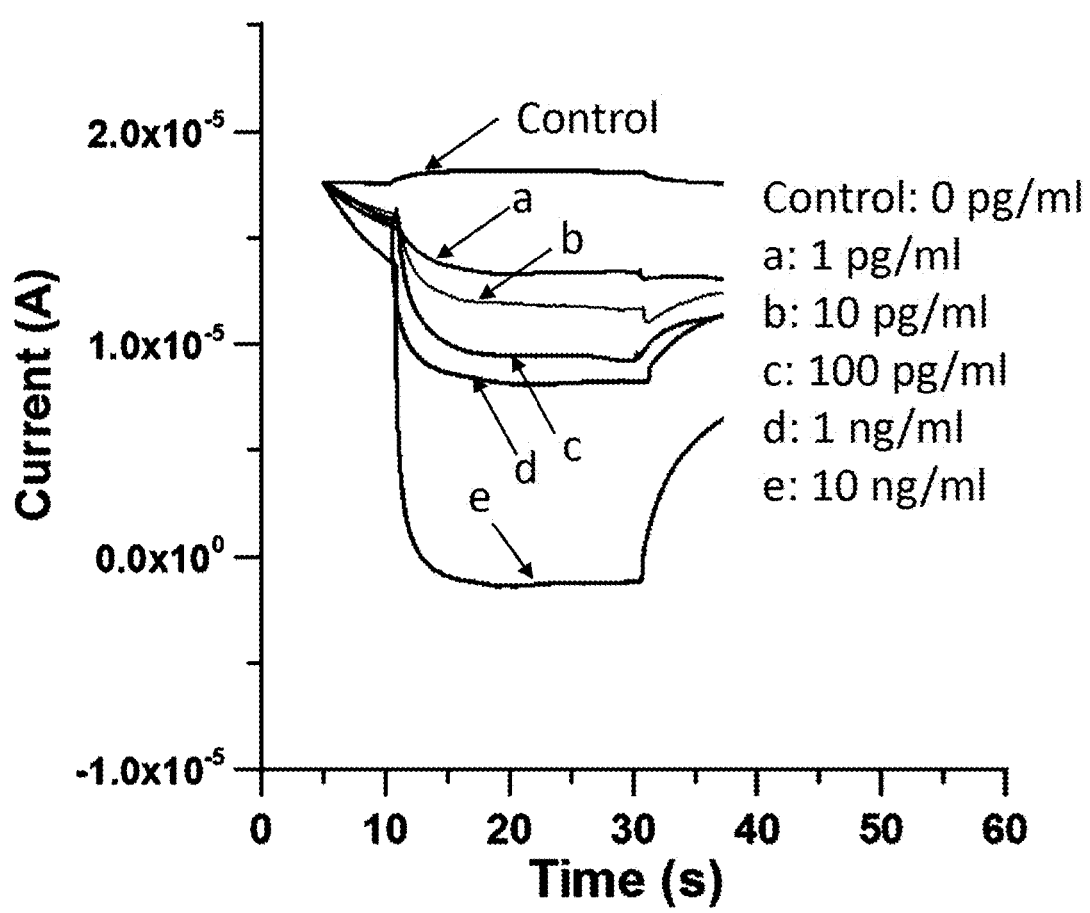
FIG. 10 is an experimental result showing an interleukin (IL-6) dose-dependent increase in electric current intensity in accordance with an embodiment of the present invention.

Referring now to FIG. 10. The embodiments of the present invention are further demonstrated to facilitate detection and quantification of a target molecule. In an experiment as shown in FIG. 10, when adding the molecular probe labeled with NGOQDs to a sandwich immunoassay for detection of IL-6, the intensity of detected current was shown to increase with the concentration of IL-6.

Figure 11:
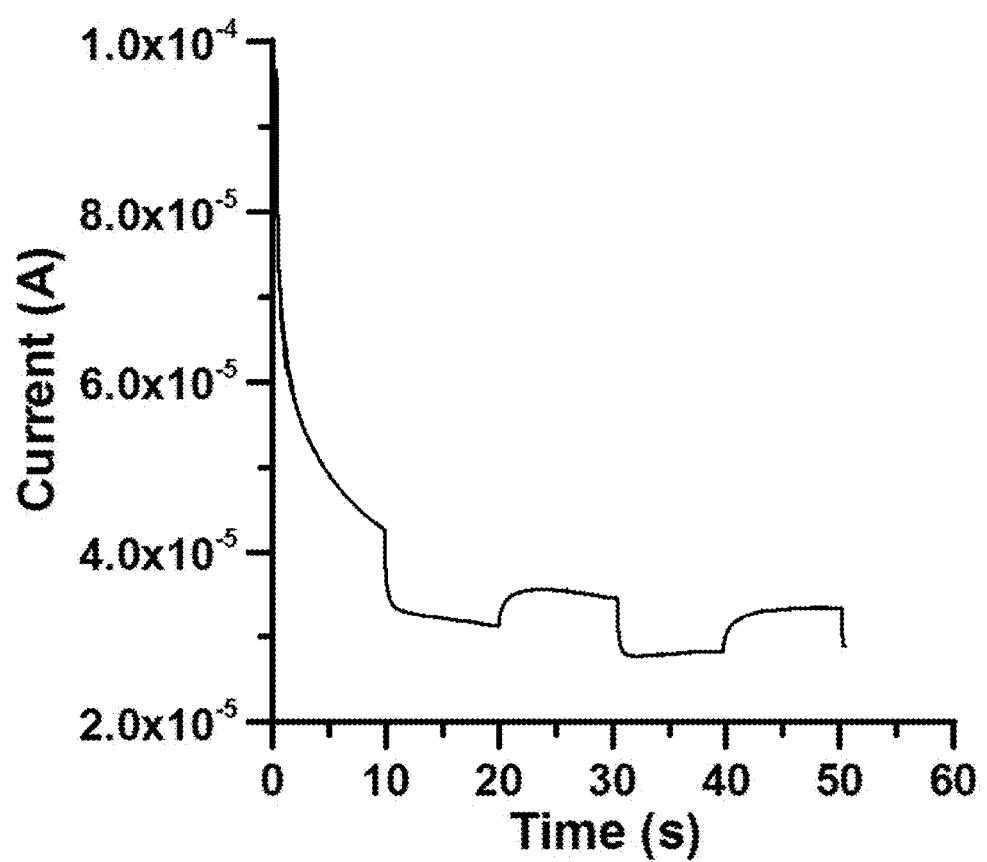
FIG. 11 is an experimental result showing the change in electric current intensity over time when light energy and chemical energy are provided in accordance with an embodiment of the present invention.

Referring now to FIG. 11. According to the embodiments of the present invention, generation of electrons by the catalyst-labeled molecular probes is demonstrated to be enhanced by providing more than one type of energy at the same time. As demonstrated in an experiment shown in FIG. 11, when 10 mM of ascorbic acid (ie. chemical energy) and intermittent light (ie. radiant energy) are both provided to a solution containing the NGOQD labeled molecular probe, electric current generated by the NGOQDs under chemical energy could be detected continuously and was shown to fluctuate according to on/off of the light energy.

Figure 12A:
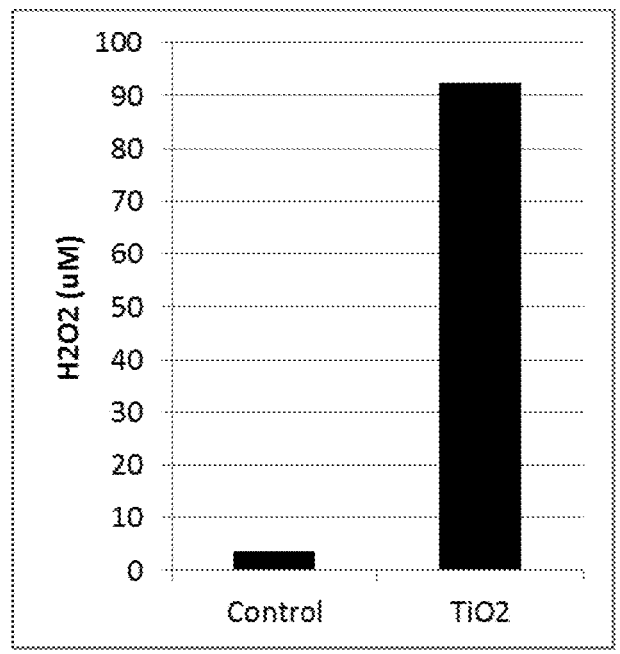
FIG. 12A is an experimental result showing the generation of $H_2O_2$ by $TiO_2$ in accordance with an embodiment of the present invention.
Figure 12B:
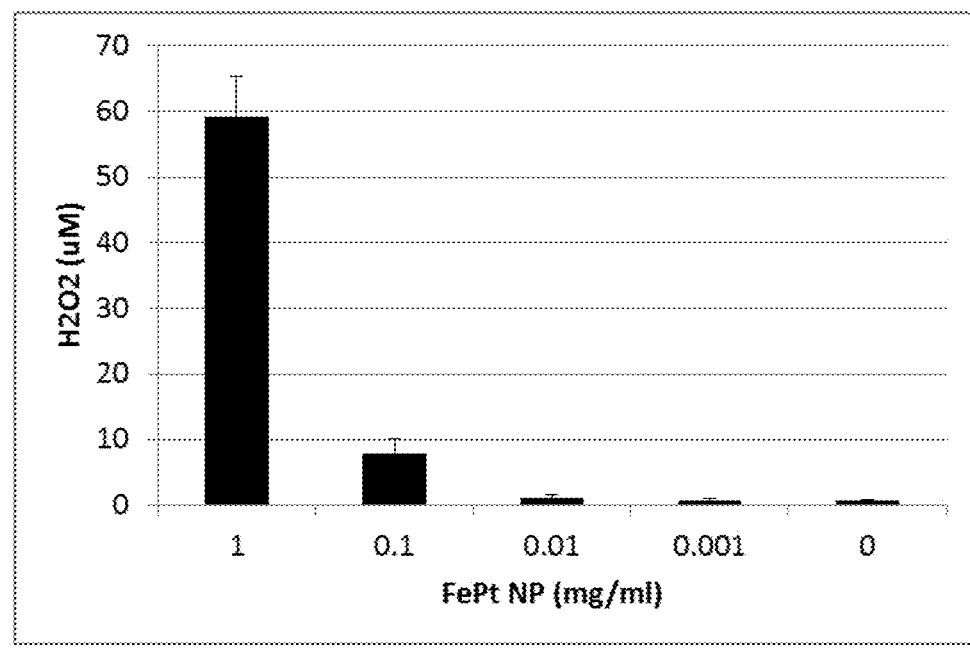
FIG. 12B is an experimental result showing a dose-dependent generation of $H_2O_2$ by FePt nanoparticles in accordance with an embodiment of the present invention.

Referring to FIGS. 12A and 12B. According to some embodiments of the present invention, the catalyst on the molecular probe may be nanoparticles or other types of quantum dots (eg. metallic semiconductor quantum dots). As demonstrated in the experiments shown in FIGS. 12A and 12B, both of $TiO_2$ and FePt nanoparticles were capable of generating $H_2O_2$ from an aqueous solution.

Figure 13:
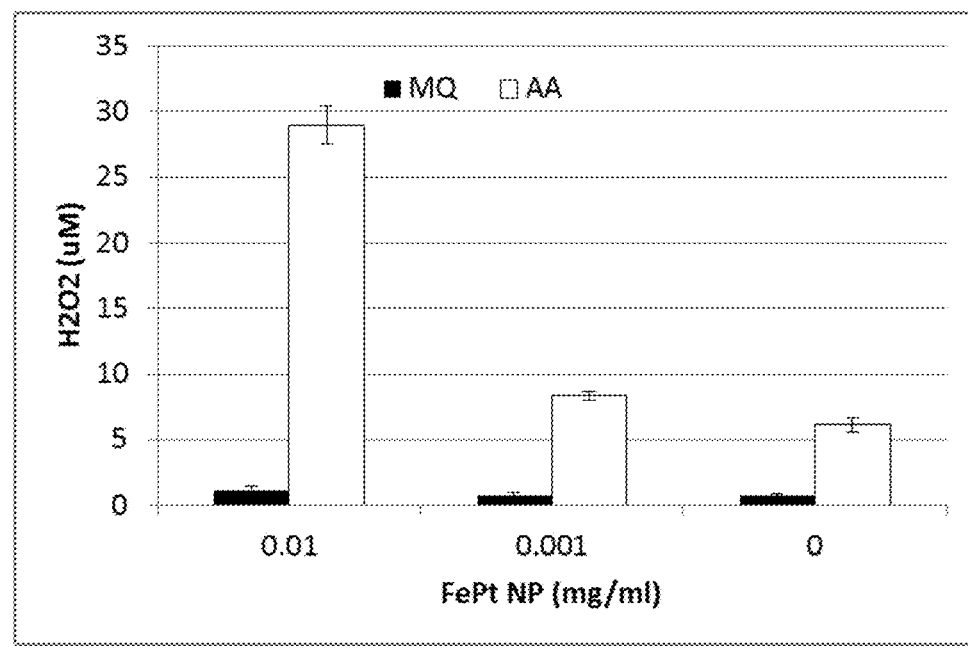
FIG. 13 is an experimental result showing the enhancement of generation efficiency of $H_2O_2$ by providing chemical energy in accordance with an embodiment of the present invention.

Referring to FIG. 13. According to some embodiments of the present invention, efficiency of mediator generation may be enhanced by providing an energy (eg. a chemical energy) to the solution. For example, the experiment shown in FIG. 13 demonstrated that providing a chemical energy by addition of ascorbic acid (denoted AA in the figure) to an aqueous solution that contains 0.01 mg/mL or 0.001 mg/mL of FePt nanoparticles resulted in significant increases in $H_2O_2$ production, as compared with the control without AA (denoted MQ in the figure). The results also showed that $H_2O_2$ generation by the FePt nanoparticles was also dose-dependent.

Figure 14:
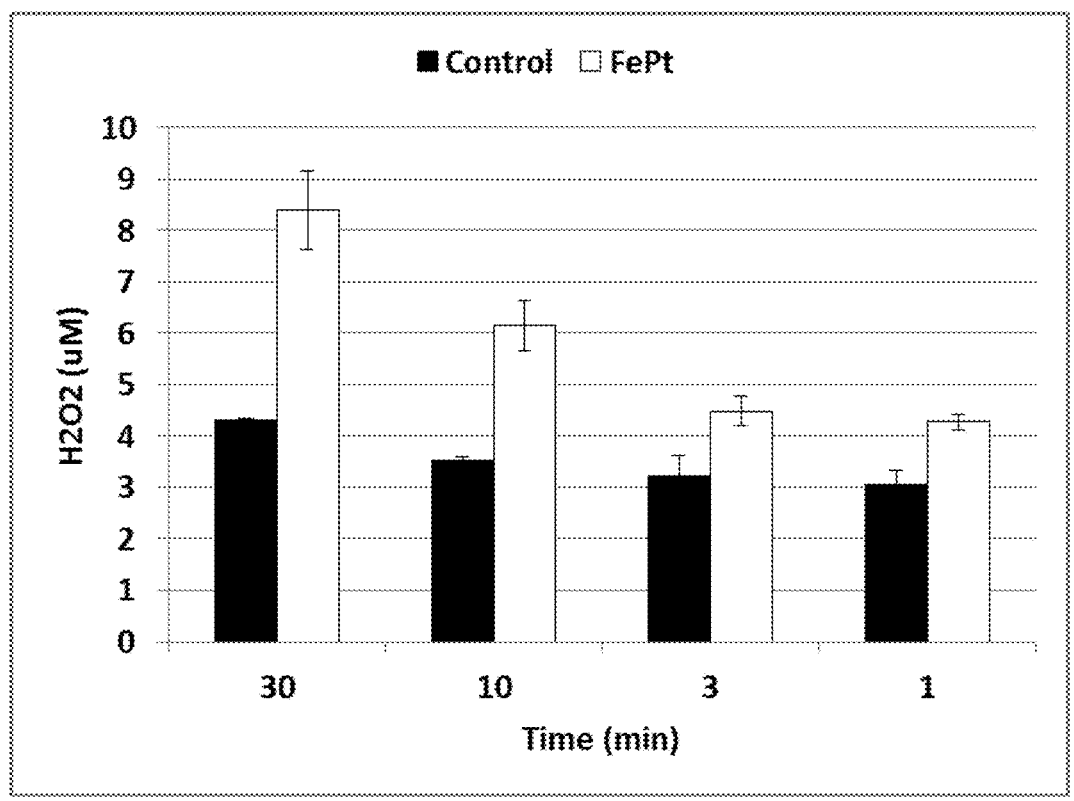
FIG. 14 is an experimental result showing the accumulation of $H_2O_2$ generated by FePt nanoparticles in accordance with an embodiment of the present invention.

Referring to FIG. 14. According to some embodiments of the present invention, the mediators generated by other types of catalyst (eg. nanoparticles) were also capable of accumulating in the solution for a period of time. As in the experiment in FIG. 14, $H_2O_2$ generated by 0.001 mg/mL of FePt nanoparticles under the presence of 2 mM of ascorbic acid was shown to accumulate to over 8 μM in water in 30 min.

In sum, the present invention according to the aforementioned embodiments amplifies detection signals or obtains amplified detection signals of molecular detection assays by labeling detector molecules with one or more catalysts that are capable of generating mediators from a solution. The mediators can stably accumulate in the solution for a period of time to continuously participate in the chemical reaction of the molecular detection assay, thereby resulting in significantly amplified signals (that is, an "one-to-many" amplification) in response to detection of the target molecule. Therefore, the present invention effectively improves the detection sensitivity of existing assays for little or reduced cost. Additionally, as the electrons and mediators can be generated simultaneously, the present invention provides at least two types of measurable signals, thus offering the possibility of reconfirming or double checking the detected signals so as to ensure accuracy of the molecular detection.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A method for assaying a target molecule, comprising the steps of:
   (a) immobilizing a capturing antibody on a sensing surface, wherein the capturing antibody specifically binds to the target molecule;
   (b) introducing an aqueous solution containing the target molecule to the sensing surface to allow binding of the target molecule to the capturing antibody;
   (c) adding a molecular probe to the introduced aqueous solution containing the target molecule on the sensing surface, wherein the molecular probe comprises
   a detector molecule that specifically binds to the target molecule, so that one end of the detector molecule is attached to the target molecule; and
   at least one label bonded to the other end of the detector molecule wherein said label is configured to function as a catalyst for generating reactive oxygen species (ROS) mediator from the solution;
   (d) providing after step (c), a sufficient radiation energy to the solution containing the added molecular probe over the sensing surface for a period of time that avows generation of the ROS mediator by the label from the solution, wherein said ROS mediator is $H_2O_2$;
   (e) introducing a reactant to the sensing surface after step (d) for initiating a chemical reaction between the reactant and the ROS mediator to generate a measurable signal; and
   (f) measuring the measurable signal generated by the chemical reaction.

2. The method according to claim 1, wherein the ROS mediators generated by the label are capable of accumulating in the solution for at least the period of time.

3. The method according to claim 1, wherein the detector molecule and the target molecule interacts with each other by selective molecular binding, and
   the selective molecular binding comprises a protein based interaction.

4. The method according to claim 1, wherein the signals comprise a change in optical properties, electromagnetic properties, thermodynamic properties or mechanical properties.

* * * * *